(12) United States Patent
Davies et al.

(10) Patent No.: US 9,658,144 B1
(45) Date of Patent: May 23, 2017

(54) SYSTEMS AND METHODS FOR CHEMICALLY TESTING A SAMPLE AND SAMPLING PROBES THEREFOR

(75) Inventors: Colin Davies, Seattle, WA (US); Paul Danilchik, Poulsbo, WA (US); Steve Gunther, Seattle, WA (US)

(73) Assignee: Brooks Rand Inc, Seattle, WA (US)

(*) Notice: Subject to any disclaimer, the term of this patent is extended or adjusted under 35 U.S.C. 154(b) by 0 days.

(21) Appl. No.: 13/150,989

(22) Filed: Jun. 1, 2011

Related U.S. Application Data

(60) Provisional application No. 61/350,391, filed on Jun. 1, 2010.

(51) Int. Cl.
*G01N 1/40* (2006.01)
*G01N 1/34* (2006.01)

(52) U.S. Cl.
CPC .............. *G01N 1/405* (2013.01); *G01N 1/34* (2013.01)

(58) Field of Classification Search
CPC ......... B01L 2200/027; B01L 3/502715; B01L 3/565; B01L 3/50825; B01L 2300/044; B01L 2200/026; B01L 2300/047; B01L 3/0293; B01L 3/5082; A61J 1/2096; A61J 2001/201; B65D 51/002; G01N 35/1079; G01N 1/405; G01N 1/34
USPC ........... 422/512, 546, 511, 561, 570; 436/81
See application file for complete search history.

(56) References Cited

U.S. PATENT DOCUMENTS

| | | | | |
|---|---|---|---|---|
| 5,012,845 A | * | 5/1991 | Averette | G01N 35/1079 141/130 |
| 5,432,098 A | * | 7/1995 | Wilks | G01N 35/1079 422/547 |
| 7,082,848 B2 | * | 8/2006 | Fjerdingstad | G01N 1/14 73/863.41 |
| 7,552,617 B2 | | 6/2009 | Danilchik | |
| 2002/0006360 A1 | * | 1/2002 | Neal | G01N 35/1097 422/501 |
| 2009/0259144 A1 | * | 10/2009 | Champseix et al. | 600/576 |
| 2011/0152926 A1 | * | 6/2011 | Vetrecin | 606/223 |

OTHER PUBLICATIONS

Modified Headspace SPME-GC Device for Sampling Volatile Compounds in Acidic Medium W.A. Araujo, C.A. Lacerda. E.A. Cappelaro, Fernando M. Lancas J. Sep. Sci. 2003, 26, 624-628.*
Monitoring Inorganic Mercury and Methylmercury Species with Liquid Chromatography-Piezoelectric Detection Beatriz Palenzuela, Lisbeth Manganiello, Angel Rios, Miguel Valcarcel Analytica Chimica Acta 511 (2004) 289-294.*

* cited by examiner

*Primary Examiner* — Krishnan S Menon
*Assistant Examiner* — Dwan A Gerido
(74) *Attorney, Agent, or Firm* — Christensen O'Connor Johnson Kindness PLLC

(57) ABSTRACT

Systems, methods, and sampling probes for chemically testing a liquid sample are provided. In accordance with one embodiment of the present disclosure, a system generally includes a sample container for containing a liquid, wherein the liquid includes a chemical compound of interest and a reducing agent, and a non-corrosive sampling probe comprising a first channel for delivering a flow of gas to the liquid sample, and a second channel for purging sample fluid from the sample container, wherein at least a portion of the sampling probe is in contact with the liquid.

14 Claims, 6 Drawing Sheets

SYSTEMS AND METHODS FOR CHEMICALLY TESTING A SAMPLE AND SAMPLING PROBES THEREFOR

CROSS-REFERENCE TO RELATED APPLICATION

This application claims the benefit of U.S. Provisional Patent Application No. 61/350,391, filed on Jun. 1, 2010, the disclosure of which is hereby expressly incorporated by reference into the present application.

BACKGROUND

Mercury is a naturally occurring element that is known to have a toxic effect on human beings and animals in very low concentrations. Mercury's high toxicity combined with its penchant for bioaccumulation make it of particular concern among heavy metals. In particular, mercury can affect the nervous system, with fetuses, infants, and children being particularly sensitive to the effects of mercury.

There are numerous automated systems for measuring mercury concentrations in a variety of sample types. In many automated mercury analysis systems, a liquid sample may be pushed or drawn from a sample vial to a purge vessel (or a gas-liquid separator), where the mercury is vaporized into a gas for analysis. This method of liquid transfer from the sample vial to the purge vessel has some drawbacks because liquid samples can easily contaminate the transfer line, as well as the purge vessel, resulting in a high bias in subsequent test results.

One system currently on the market purges the liquid sample directly in the test vial, instead of in the purge vessel. However, the sample vials are placed in this system as open containers, and only plugged immediately prior to purging. These open containers are therefore subject to contamination from mercury present in the surrounding air and dust. In low level mercury analysis, preventing contamination of the samples from atmospheric mercury is critical to obtain reliable measurements of mercury in native samples. To mitigate potential contamination, open vial systems are generally operated in a clean room environment, a clean hood, or a hepa-filtered enclosure, all of which add significant costs. In reality, however, these "clean" environment solutions only eliminate particulate mercury in airborne dust, and even air free of particulates still may have a measurable amount of gaseous mercury that can impact results.

Therefore, there exists a need for an improved closed vial analytical system for total mercury analysis that prevents contamination from air and dust, as well as contamination in the transfer line and purge vessel. In order to accomplish this, a septa piercing sampling probe that is non-corrosive to acid is required.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with one embodiment of the present disclosure, a system for chemically testing a liquid sample is provided. The system generally includes a sample container for containing a liquid, wherein the liquid includes a chemical compound of interest and a reducing agent. The system further includes a non-corrosive sampling probe comprising a first channel for delivering a flow of gas to the liquid sample, and a second channel for purging sample fluid from the sample container, wherein at least a portion of the sampling probe is in contact with the liquid.

In accordance with another embodiment of the present disclosure, a method for chemically testing a liquid sample is provided. The method generally includes obtaining a sample container containing a liquid, wherein the liquid includes a chemical compound of interest and a strong acid. The method further includes submerging at least a portion of a sampling probe in the liquid, wherein the sampling prove is a non-corrosive probe comprising a first channel for delivering a flow of gas to the liquid sample and a second channel for receiving sample fluid and purging the sample fluid from the sample container.

In accordance with another embodiment of the present disclosure, a sampling probe for chemically testing a liquid sample including mercury and a reducing agent, wherein the reducing agent is a strong acid, is provided. The sampling probe includes an elongate body having at least first and second channels, the first channel configured for delivering a flow of gas to the liquid sample, the second channel for receiving sample fluid, wherein the sampling probe is non-metallic.

DESCRIPTION OF THE DRAWINGS

The foregoing aspects and many of the attendant advantages will become more readily appreciated by reference to the following detailed description, when taken in conjunction with the accompanying drawings, wherein.

DETAILED DESCRIPTION

The detailed description set forth below in connection with the appended drawings where like numerals reference like elements is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result.

The following discussion proceeds with reference to examples of systems for testing chemical levels (e.g., mercury levels) in a test sample and components therefor. Several examples of the present disclosure are directed to systems that employ a "closed vial" technique for volatilizing chemical components in the sample container or vial and extracting such components therefrom for subsequent testing and/or analysis. Examples of sampling probes suitable for use in various testing systems will also be described. While several embodiments described herein are directed to systems that detect and/or analyze total mercury, it will be appreciated that aspects of the disclosed subject matter have wide application, and therefore, such systems and components therefor may be suitable for use in other applications, such as testing systems that test for volatilized compounds other than mercury, etc. Accordingly, the following descriptions and illustrations herein should be considered illustrative in nature, and thus, not limiting the scope of the disclosed subject matter.

In the following description, numerous specific details are set forth in order to provide a thorough understanding of exemplary embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Figure 1:
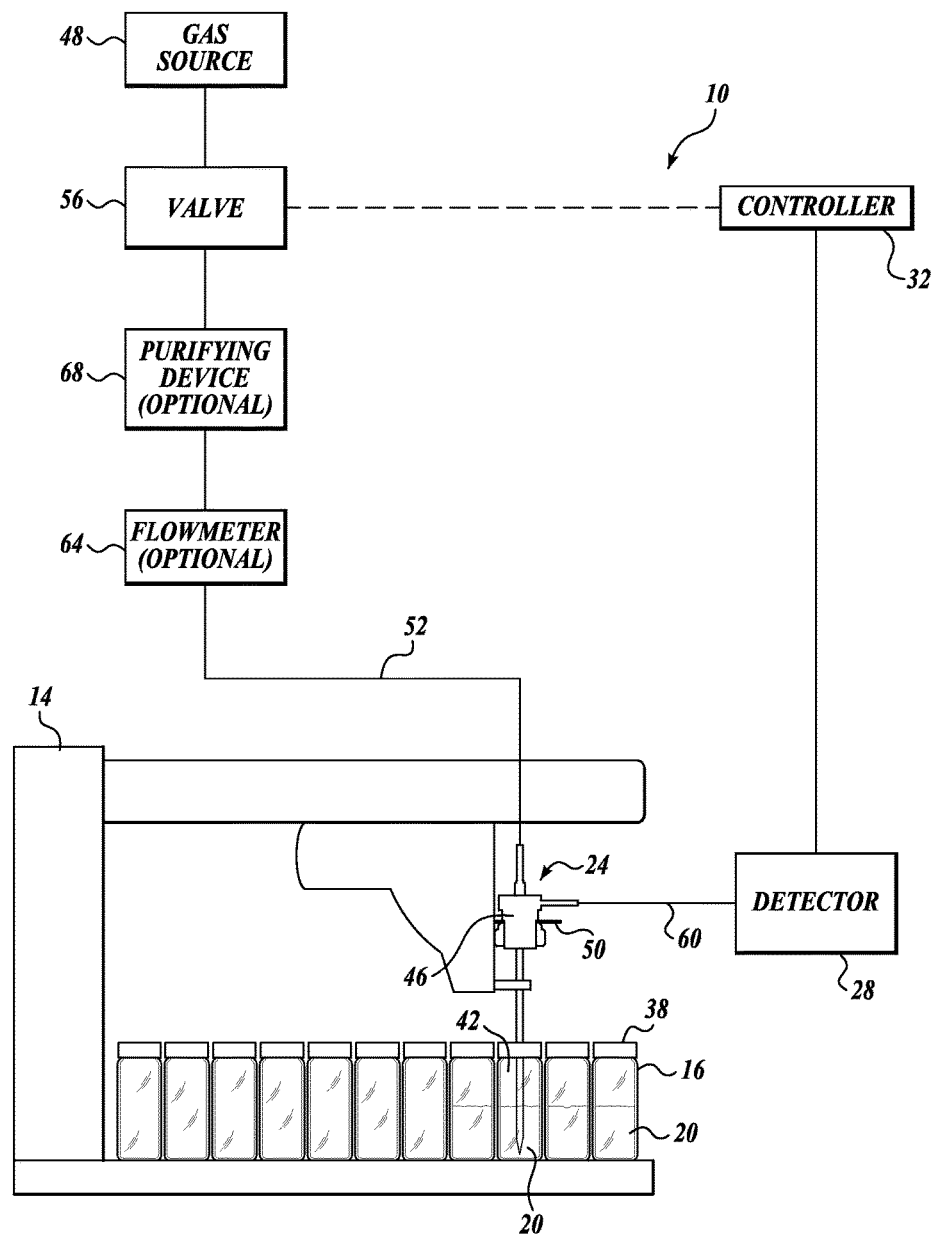
FIG. 1 is a schematic diagram of one example of a chemical testing system formed in accordance with aspects of the present disclosure.

Turning now to FIG. 1, in accordance with one embodiment, a system 10 is shown for processing and/or detecting low levels of a chemical compound, such as mercury. As best shown in FIG. 1, the system 10 may includes a holder in the form of an autosampler 14 for carrying a plurality of sample containers 16 each containing a test solution 20, a purging assembly 24 for extracting test solution volatiles from the test solution 20, and a detector 28 for detecting and/or analyzing levels of a chemical compound of interest present in a test sample. One or more components of the system 10 may be controlled by a controller 32.

It will be appreciated that several components of the system 10 described herein are in fluid (e.g., liquid, gas, etc.) communication with one another, for example, by way of a plurality of tubular members. Tubular members may be formed from, but are not limited to, a fluoropolymer, such as TEFLON® tubing.

Sample container(s) 16 may be, but is not limited to, a sealable autosampler vial. To prepare the test solution 20 in one embodiment, a test sample, such as a liquid believed to contain a chemical compound of interest, such as mercury, a mercury standard, or a blank such as water, is mixed with an oxidizing agent so as to oxidize any form of mercury present in the test sample into oxidized or divalent mercury ($Hg^{2+}$). This mixture is then added to the sample container 16 and mixed with a reducing reagent, such as stannous chloride ($SnCl_2$), to reduce the oxidized mercury ($Hg^{2+}$) into elemental mercury ($Hg^0$). In one embodiment, the test sample may be pre-reduced with another reducing reagent, such as hydroxyalamine hydrochloride. In other embodiments, the test samples are prepared according to EPA method 1631 or EPA method 245.7.

The reducing agent may be a strong acid. As a non-limiting example, after the addition of the reducing agent, the pH in the sample container may be less than or equal to about 7. As another non-limiting example, after the addition of the reducing agent, the pH in the sample container may be less than or equal to about 2.

After the test solution 20 is prepared in the sample container 16, the sample container 16 is then capped and sealed, for example with a cap 38, and loaded into the autosampler 14. It should be appreciated that the sample may be prepared and capped in a "clean" environment such as clean room, a clean hood, or a hepa-filtered enclosure to prevent sample contamination. In embodiments where the chemical compound of interest is mercury, because the sample container 16 is sealed, no volatile mercury can escape the sample container 16, and no atmospheric mercury can enter the container 16. As such, the total amount of mercury in the container 16 is stable for many hours before the test solution is purged and transferred to the detector 28. It will be appreciated that the quantity of test solution in the container 16 may be selected so as to provide a head space 42 between the cap 38 and the level of the test solution 20 contained in the container 16.

In one embodiment, the sample container 16 may be capped and sealed with a standard septa cap. For example, the septa cap may be a PTFE/Silicon septa cap having a thickness of between 1.5 mm and 3 mm, although other septa caps may be practiced with the subject matter of the present disclosure.

Still referring to FIG. 1, the system 10 further includes a purging assembly 24. The purging assembly 24 includes a sampling probe 46 and a source 48 of pressurized inert gas, such as argon. In one embodiment, the sampling probe 46 is adapted to be removable coupled with a support arm 50 (see also FIG. 2) of the autosampler 14. As shown in FIGS. 1 and 3, the sampling probe 46 delivers a purge gas from the gas source 48 to the test solution 20 in sealed container 16 via line 52. In the illustrated embodiment, the sample container 16 is configured as a gas and liquid separator. In that regard, the purge gas delivered to the test solution 20 purges the test solution in the container 16, thereby stripping test solution volatiles 54 to the headspace 42. The sampling probe 46 then removes or extracts the test solution volatiles 54 present in the head space 42 and delivers the test solution volatiles to the detector 28 via line 60.

In another embodiment, the source 48 of gas may be used to transfer the liquid sample through the probe to a separate gas and liquid separator.

The purge gas from the gas source 48 can be conditionally delivered to the sampling probe 46 via controllable valve 56. Before the gas from gas source 48 reaches sample container 16, it may optionally pass through at least one flow control device or flowmeter 64 for measuring and/or controlling the flow rate of the gas. The flow meter 64 may be, but is not limited to, a mass flow controller or a rotameter. Gas from gas source 48 may also optionally pass through at least one purifying device 68 to eliminate any undesirable compounds, such as mercury, that may be present in the gas. In one embodiment, the purifying device 68 may be, but is not limited to, a gold cleanup column.

The sampling probe 46 enters the sample container 16. In that regard, the sampling probe may pierce the cap 38 of the sample container 16. In another embodiment, the cap 38 may enter the sample container 16 without piercing the cap 38. As a non-limiting example, the cap 38 may be removed and the sampling probe 46 may be formed with a new sealing cap that covers the container 16. As the sampling probe 46 enters the sample container 16, the new sealing cap forms a seal with the sample container 16.

In prior art systems, a stainless steel septum piercing needle assembly has been used for entering the sample container 16 and transferring the test solution from the sample container 16. However, in embodiments such as for total mercury analysis, the liquid samples are very acidic and corrosive when purged, thus making the use of a probe having exposed metal portions infeasible. In that regard, in accordance with embodiments of the present disclosure, the sampling probe 46 is non-corrosive and non-degradable in a strong acid For example, the probe may be non-metal, or, if the probe 46 is metal, the metal portions may be coated with a non-metallic coating.

In one embodiment, the sampling probe 46 is a plastic inert sample probing that is sharp enough and rigid enough to pierce through the septa cap 38, inert enough to withstand the corrosive conditions present in the container 16, and does not contaminate the test solution when it comes in contact therewith. In one embodiment, the material for the sampling probe 46 is polyether ether ketone (PEEK). Other non-corrosive materials having sufficient rigidity may also be used, including but not limited to glass or other plastics that are able to withstand strong acid conditions.

In another embodiment, the sampling probe 46 may be a metal probe, for example, a stainless steel probe, that is coated with a non-metallic, non-corrosive an non-degradable coating that is able to withstand the strong acid conditions present in the container. In that regard, all portions of the probe that come into contact with the liquid in the vial are coated. Suitable coatings include the following: thermoplastic (fluoropolymer, polyethylene, etc.), silicon (amorphous, crystalline, and silicon compounds, such as silicon nitride, impregnated silicon, etc.), epoxy, acrylic coatings, and combinations thereof.

Figure 2:
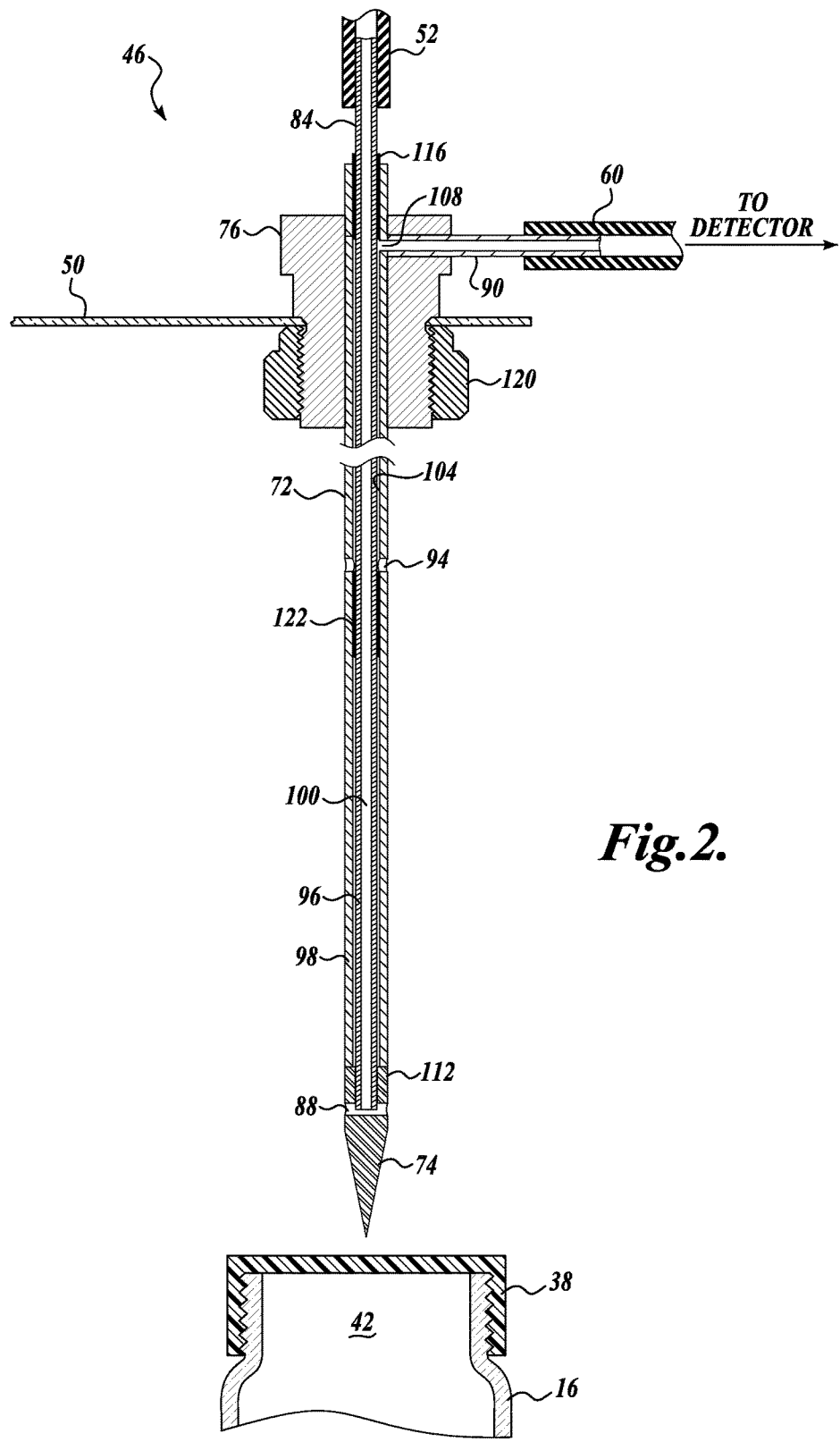
FIG. 2 is a cross-sectional view of several components of a purging assembly shown in FIG. 1, including a sampling probe disposed in a default position.
Figure 3:
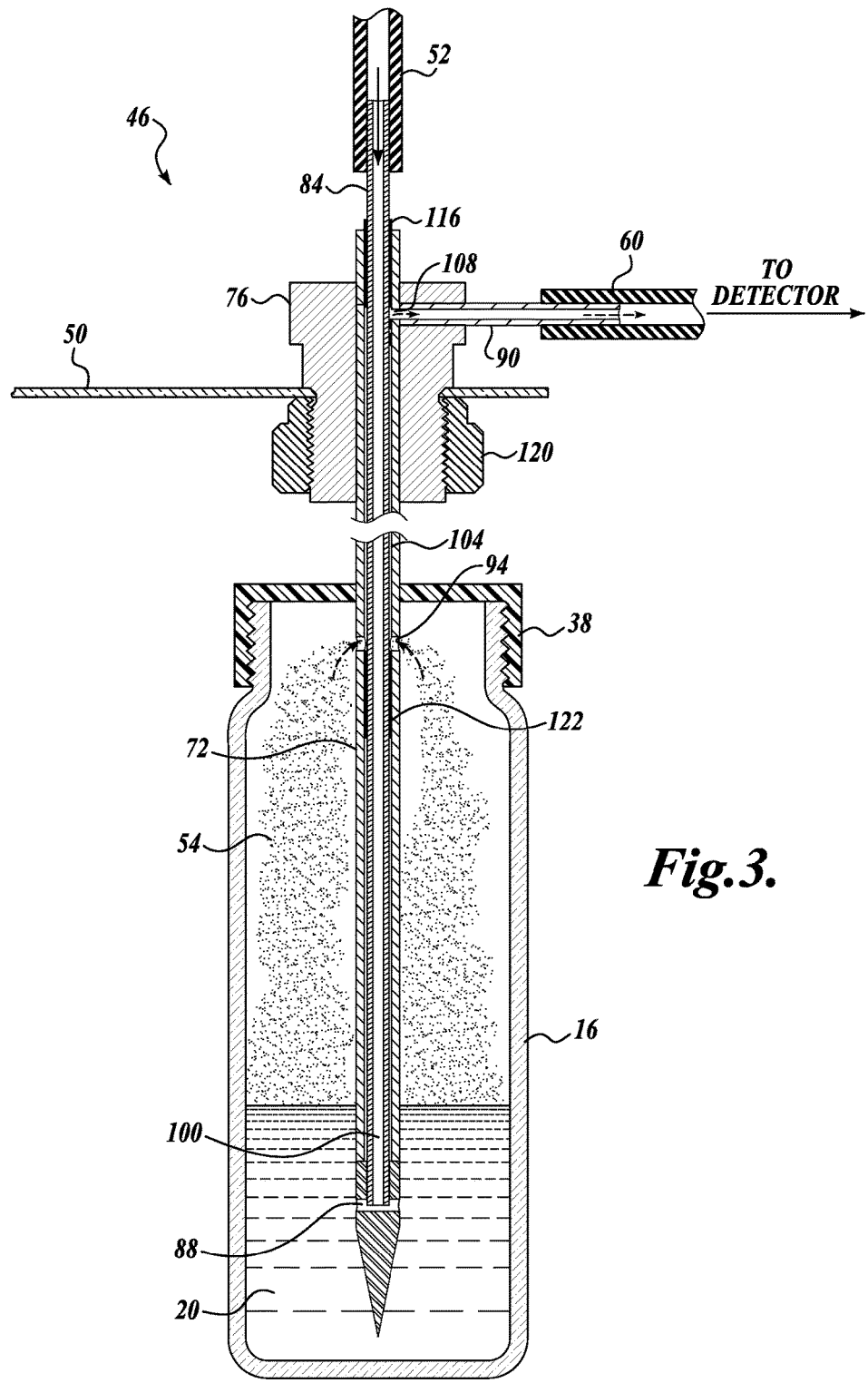
FIG. 3 is a cross sectional view of the sampling probe through the cap of the sample container.

One example of the sampling probe 46 constructed in accordance with aspects of the present disclosure is shown in FIGS. 2 and 3. As best shown in FIG. 2, the sampling probe 46 includes an elongated needle 72 having a sharpened tip 74 at its distal end and a fitting 76 fixedly attached near the proximal end of the needle 72. The sampling probe 46 also includes a purge gas inlet pipe 84 formed at the proximal end of the needle 72 and connected in fluid communication with a purge gas port 88. In the embodiment shown, the purge gas port 88 is disposed near the distal end of the needle 72. The sampling probe 46 also includes an outlet pipe 90 mounted to the fitting 76, and connected in fluid communication with a test solution volatiles port 94.

In the embodiment shown in FIG. 2, the needle 72 includes inner and outer coaxially arranged tubes 96 and 98. The inner tube 96 extends past the outer tube 98 at the proximal end of the sampling probe 46, thereby forming the purge gas inlet pipe 84. As such, the inner tube 96 forms a gas delivery channel 100 that extends from a port defined by the purge gas inlet pipe 84 and opens into the purge gas port 88. As best shown in FIGS. 2 and 3, the outer surface of the inner tube 96 is spaced from the inner surface of the outer tube, thereby forming a cavity 104 therebetween. The cavity 104 or a section thereof connects the test solution volatiles port 94 in fluid communication with the outlet pipe 90. In the embodiment shown, the outlet pipe 90 is mounted within a bore of the fitting 76 such that its inner end is disposed adjacent to and in fluid communication with the cavity 104 via aperture 108. At the distal end of the needle 72 just proximate the purge gas port 88, a first seal 112 is provided to close off and seal the lower end of the cavity 104. Similarly, at the proximal end, a second seal 116 is provided to close off and seal the upper end of cavity 104. The seals 112 and 116 can be formed by epoxy, polyurethane, or other non-corrosive materials. The seals further maintain the position of the inner tube 96 with respect to the outer tube 98.

As briefly described above, the sampling probe 46 can be removably mounted to a support arm 50 of the autosampler 14 via an attachment assembly. In the embodiment shown in FIGS. 2 and 3, the attachment assembly is formed by a portion of the fitting 76 and a cooperating threaded nut 120. In one embodiment, the support arm 50 is mounted to or otherwise coupled to a Z-axis actuator that translates the sampling probe 46 vertically between a start or default position shown in FIG. 2 and a septa inserted position shown in FIG. 3.

Figure 6:
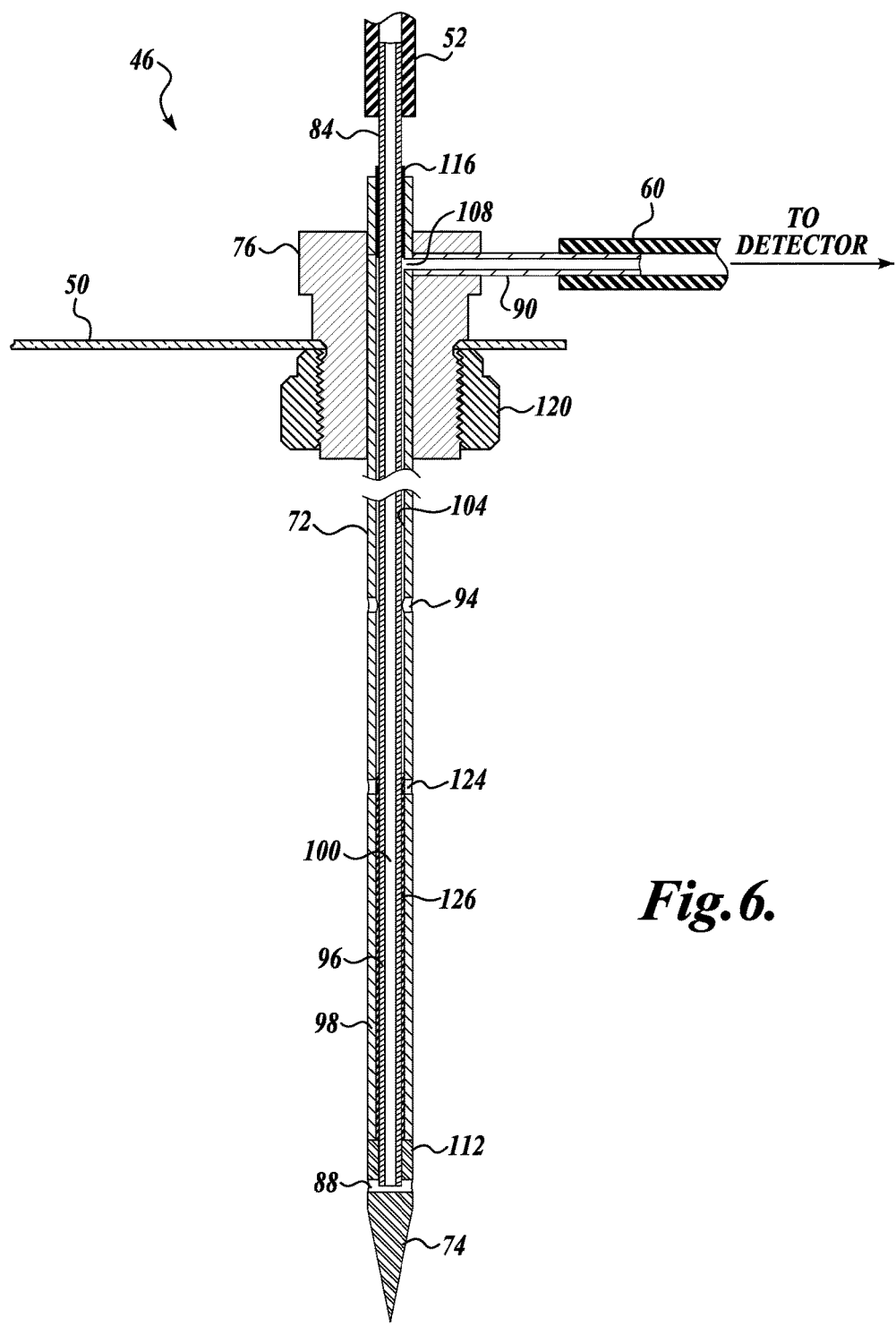
FIG. 6 is another embodiment of a sampling probe formed in accordance with aspects of the present disclosure.

As further shown in FIGS. 2 and 3, the sampling probe 46 may further include a seal 122, such as an o-ring, disposed just below the test solution volatiles port 94 so as to limit the length of the cavity 104. In use, the seal prevents any of the test solution volatiles from flowing distally of the seal 122. Alternatively, as best shown in FIG. 6, the sampling probe 46 may include one or more additional ports 124 for injecting a material 126, such as cyanoacrylate gel, epoxy, silicon, polyurethane foam, etc., in injectable form into a portion of the cavity 104. In one embodiment, the material 126 is injected into the port 124 through a capillary luer needle. Once injected, the material 126 cures or hardens, thereby forming a seal that defines the lower end of the cavity 104.

In use, once the sampling probe 46 has pierced the cap 38 or otherwise entered the container 16, as shown in FIG. 3, the controller 32 opens the valve 56 so as to supply a pressurized gas (e.g., argon) to line 52. Purge gas is then passed from line 52 into channel 100 via the purge gas inlet pipe 84. The purge gas is then injected into the test solution 20 within sample container 16 via the purge gas port 88. The resulting gas entering sample container 16 purges the test solution 20 to volatilize chemical components, such as mercury, present in the test solution 20, thereby releasing test solution volatiles 54 in head space 42. Due to the sealed sample container 16 and the pressurized purge gas, the test solution volatiles 54, such as argon gas and elemental mercury, exit the sealed sampler container 16 by way of the test solution volatiles port 94, the cavity 104, and the outlet pipe 90. The test solution volatiles 54 then exit the outlet pipe 90 and are transferred via line 60 to the detector 28 for detection and/or analysis.

Figure 4:
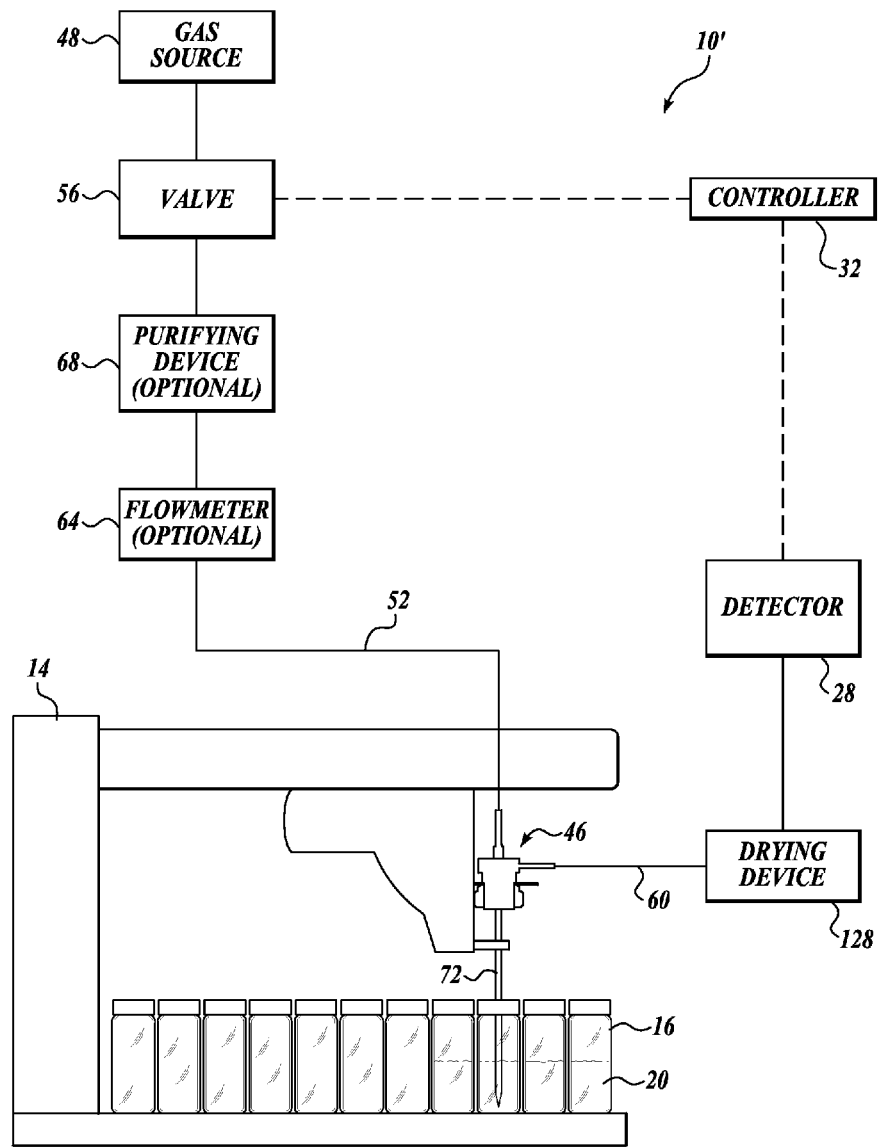
FIG. 4 is a schematic diagram of another example of a chemical testing system formed in accordance with aspects of the present disclosure.

In embodiments of the present disclosure, the detector 28 may be an atomic absorption spectrophotomer (AAS), an atomic fluorescence spectrophotometer (CVAFS), or any number of other instrument types capable of detecting the chemical compound of interest, such as mercury, in a gas stream. One spectrophotometer suitable for use with the system 10 includes, but is not limited to, a cold vapor atomic fluorescence spectrophotometer (CVAFS) as described in U.S. Pat. No. 5,731,873. The detector 28 may optionally be connected to a pollution control device (not shown), such as an iodated carbon column. In the embodiment shown in FIG. 4. the test solution volatiles, including, for example, volatilized mercury, may pass through a drying device 128, such as one or more drying membranes, to remove moisture from the gas, prior to detection and analysis by the detector 28.

Figure 5:
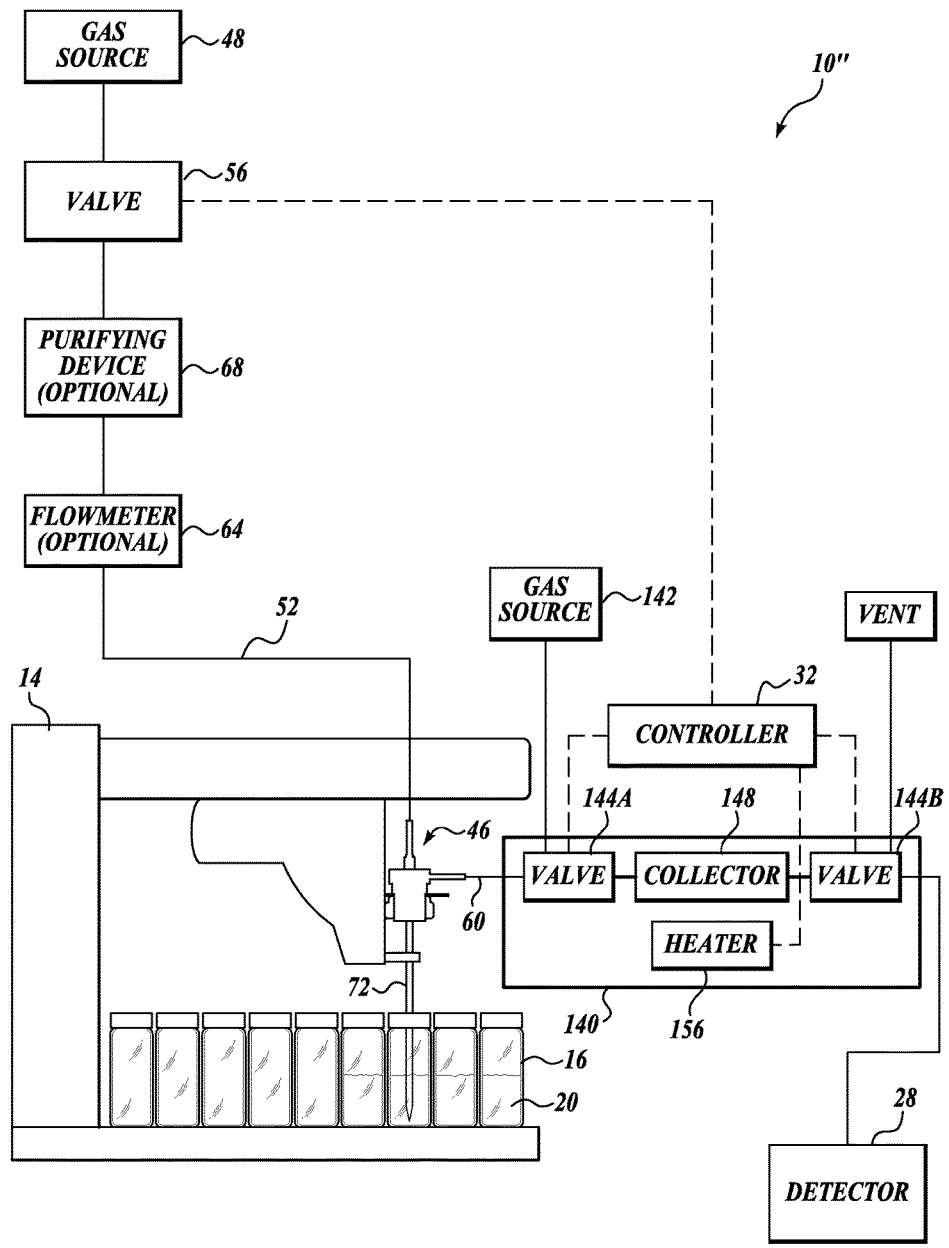
FIG. 5 is a schematic diagram of yet another example of a chemical testing system formed in accordance with aspects of the present disclosure.

In another embodiment, shown best in FIG. 5, the test solution volatiles 54 are passed through a collector assembly 140 prior to detection and/or analysis by the detector 28. The collector assembly 140 functions to concentrate the volatilized chemical compound present in the gas stream. In the embodiment shown, the collector assembly 140 is disposed in communication with a pressurized source 142 of inert gas, and includes one or more controllable valves 144 and a collector 148.

As best shown in FIG. 5, the test solution volatiles 54 exit sample container 16, passes through the controllable valve 144A, and enters collector 148. The collector 148 is capable of performing the collection (adsorption) and/or thermal desorption of the chemical compound of interest, such as mercury, and may be constructed of PYREX®, glass, quartz, or other suitable materials. The collector 148, which contains at least one trapping material for collecting, adsorbing, or trapping the volatile compounds, such as mercury, may be connected to a heat source 156, and optionally a cooling system (not shown), such as a cooling fan. In systems for testing mercury, any trapping material known in the art that is capable of efficiently trapping mercury, such as gold or platinum, may be employed in the collector 148.

The inert gas carrier from the gas source 142 may be, but is not limited to, argon, helium, neon, krypton, xenon, or radon. In one embodiment, the inert gas carrier is argon. In the illustrated embodiment of FIG. 5, the inert gas carrier from source 142 enters the collector 148 by way of the controllable valve 144A. The gas carrier may pass through a flow control device (not shown) and an optional purifying device (not shown) if desired. The chemical compound of interest, such as mercury, released from the trapping material in collector 148 are mixed with the inert gas carrier, and the resulting mixture exits the collector 148, passes through controllable valve 144B, and is delivered to detector 28.

In the illustrated embodiment of FIG. 5, the valves 144, the heat source 156, and any optional cooling device (not shown) are in electronic communication with the controller 32. In one embodiment, the controller 32 may be connected to a computer system suitable for the control and automation of system 10.

Other embodiments of systems for collecting, transferring, detecting, and analyzing volatilized chemical compounds are contemplated to be within the scope of the present disclosure. For example, a system substantially similar to the systems described above may include at least three collectors to enable continuous sample processing. Systems containing multiple collectors, sometimes referred to as trapping vessels, and the operation of such systems is described in greater detail in U.S. Pat. No. 7,552,617, issued Jun. 30, 2009, and assigned to Brooks Rand Labs, LLC, the disclosure of which is expressly incorporated by reference.

While the preferred embodiment of the disclosure has been illustrated and described, it will be appreciated that various changes can be made therein without departing from the spirit and scope of the present disclosure.

The embodiments of the disclosure in which an exclusive property or privilege is claimed are defined as follows:

1. A system for chemically testing a liquid sample, the system comprising:
   (a) a sample container containing a liquid, wherein the liquid includes chemical compound of interest and a reducing agent, wherein the reducing agent is in a strong acid solution having a pH of less than or equal to about 2; and
   (b) a sampling probe mated with the sample container to form a seal with the sample container to prevent air exchange between the sample container and an ambient environment, wherein the sampling probe is non-corroding in a solution having a pH of less than or equal to about 2, the sampling probe comprising a first channel for delivering a flow of gas to the liquid sample, and a second channel for purging sample fluid from the sample container, wherein at least a portion of the sampling probe is in contact with the liquid, wherein the first and second channels are formed from inner and outer tubes, wherein the inner tube is disposed within the outer tube, and wherein a plurality of epoxy or polyurethane seals between the inner and outer tubes define the first and second channels and maintain the positioning of the inner tube with respect to the outer tube.

2. The system of claim 1, wherein the purged sample fluid is liquid.

3. The system of claim 1, wherein the purged sample fluid is gas.

4. The system of claim 1, wherein the sample container is sealed.

5. The system of claim 1, wherein the sample container is sealable.

6. The system of claim 1, wherein the sampling probe is non-metallic.

7. The system of claim 1, wherein the sampling probe is made from polyether ether ketone.

8. The system of claim 1, wherein the sampling probe is metallic and at least the portion of the sampling probe that contacts liquid has a coating selected from the group consisting of thermoplastic, silicon, silicon compounds, epoxy, acrylic, and combinations thereof.

9. The system of claim 1, wherein the sampling probe pierces the sample container.

10. The system of claim 1, wherein the sampling probe enters the sample container.

11. The system of claim 1, wherein the chemical compound of interest is mercury.

12. A sampling probe system for chemically testing a liquid sample including mercury and a reducing agent, wherein the reducing agent is in a strong acid solution having a pH of less than or equal to about 2, the sampling probe system comprising:
   a sample container containing a liquid, wherein the liquid includes chemical compound of interest and a reducing agent, wherein the reducing agent is in a strong acid solution having a pH of less than or equal to about 2;
   a sampling probe having an elongate body mated with the sample container to form a sealed container to prevent air exchange between the sample container and an ambient environment, the elongate body having a first channel including an inlet to the sample container and a second channel including an outlet from the sample container, the inlet configured for delivering a flow of gas to the liquid sample, the second channel for delivering all sample fluid from the sample container to a detector, wherein the sampling probe is non-metallic and non-corroding in a solution having a pH of less than or equal to about 2, wherein the first and second channels are formed from inner and outer tubes, wherein the inner tube is disposed within the outer tube, and wherein a plurality of epoxy or polyurethane seals between the inner and outer tubes define the first and second channels and maintain the positioning of the inner tube with respect to the outer tube.

13. The sampling probe of claim 12, wherein the sampling probe is made from polyether ether ketone.

14. A system for chemically testing a liquid sample, the system comprising:
   (a) a sample container for containing a liquid, wherein the liquid includes mercury and a reducing agent, wherein the reducing agent is in a strong acid solution having a pH of less than or equal to about 2;
   (b) a sampling probe mated with the sample container to form a seal to prevent air exchange between the sample container and an ambient environment, wherein the sampling probe is non-corroding in a solution having a pH of less than or equal to about 2, the sampling probe comprising a first channel for delivering a flow of gas to the liquid sample, and a second channel for purging sample fluid from the sample container, wherein at least a portion of the sampling probe is in contact with the liquid, wherein the material of the sampling probe is selected from the group consisting of non-metallic, polyether ether ketone, and metallic with a coating selected from the group consisting of thermoplastic, silicon, silicon compounds, epoxy, acrylic, and combinations thereof, wherein the first and second channels are formed from inner and outer tubes, wherein the inner tube is disposed within the outer tube, and wherein a plurality of epoxy or polyurethane seals between the inner and outer tubes define the first and second channels and maintain the positioning of the inner tube with respect to the outer tube; and (c) a detector in fluid communication with the sample container and the sampling probe for receiving all of the purged sample fluid from the sample container and detecting a volatile chemical compound of interest from the purged sample fluid.

\* \* \* \* \*